(12) United States Patent
Shi et al.

(10) Patent No.: US 11,826,447 B2
(45) Date of Patent: Nov. 28, 2023

(54) ALGINATE DENTIFRICE COMPOSITIONS AND METHODS OF MAKING THEREOF

(71) Applicant: Colgate-Palmolive Company, New York, NY (US)

(72) Inventors: Manying Shi, Guangzhou (CN); Yun Xu, Langhorne, PA (US); Yuan Wu, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 4 days.

(21) Appl. No.: 16/099,734

(22) PCT Filed: May 10, 2016

(86) PCT No.: PCT/CN2016/081558
§ 371 (c)(1),
(2) Date: Nov. 8, 2018

(87) PCT Pub. No.: WO2017/193284
PCT Pub. Date: Nov. 16, 2017

(65) Prior Publication Data
US 2019/0151209 A1 May 23, 2019

(51) Int. Cl.
*A61K 8/27* (2006.01)
*A61Q 11/00* (2006.01)
*A61K 8/25* (2006.01)
*A61K 8/73* (2006.01)
*A61K 8/29* (2006.01)
*A61K 8/19* (2006.01)
*A61K 8/365* (2006.01)
*A61K 8/21* (2006.01)

(52) U.S. Cl.
CPC .................. *A61K 8/27* (2013.01); *A61K 8/19* (2013.01); *A61K 8/21* (2013.01); *A61K 8/25* (2013.01); *A61K 8/29* (2013.01); *A61K 8/365* (2013.01); *A61K 8/733* (2013.01); *A61Q 11/00* (2013.01); *A61K 2800/28* (2013.01); *A61K 2800/805* (2013.01)

(58) Field of Classification Search
None
See application file for complete search history.

(56) References Cited

U.S. PATENT DOCUMENTS

| 3,935,305 | A | * | 1/1976 | Delaney | A61K 8/19 424/49 |
| 4,992,259 | A | * | 2/1991 | Schiraldi | A61Q 11/00 424/49 |
| 5,000,944 | A | | 3/1991 | Prencipe et al. | |
| 5,780,015 | A | | 7/1998 | Fisher et al. | |
| 5,880,076 | A | * | 3/1999 | Vermeer | C11D 3/0089 510/123 |
| 5,885,551 | A | * | 3/1999 | Smetana | A61K 6/20 424/49 |
| 8,865,192 | B2 | * | 10/2014 | Swaine, Jr. | A61K 8/35 424/401 |
| 9,095,530 | B2 | | 8/2015 | Won et al. | |
| 10,064,794 | B2 | | 9/2018 | Xu et al. | |
| 10,555,880 | B2 | | 2/2020 | Shi | |
| 2004/0146466 | A1 | * | 7/2004 | Baig | A61K 6/20 424/49 |
| 2007/0071695 | A1 | * | 3/2007 | Chopra | A61K 8/25 424/53 |
| 2012/0308488 | A1 | | 12/2012 | Pilch et al. | |
| 2013/0216485 | A1 | | 8/2013 | Campbell et al. | |
| 2013/0224270 | A1 | | 8/2013 | Robinson et al. | |
| 2014/0127142 | A1 | | 5/2014 | Takahashi et al. | |
| 2016/0000667 | A1 | * | 1/2016 | Potnis | A61K 8/27 424/401 |
| 2016/0346185 | A1 | | 12/2016 | Lv et al. | |
| 2017/0135936 | A1 | * | 5/2017 | Shanmugam | A61K 8/27 |

FOREIGN PATENT DOCUMENTS

| CN | 102204874 | | 10/2011 |
| CN | 102204874 | B * | 6/2012 |
| CN | 103006529 | | 4/2013 |
| CN | 103405362 | A | 11/2013 |
| WO | 1994/26245 | | 11/1994 |
| WO | 2002/45678 | | 6/2002 |

OTHER PUBLICATIONS

International Search Report and Written Opinion of the International Searching Authority in International Application No. PCT/US2016/081558, dated Jul. 6, 2016.
CN103006529, Chen Yongan, "Toothpaste capable of stopping infection of decayed tooth," Apr. 3, 2013, English language machine translation of abstract, Espacenet, date obtained: Jul. 21, 2021, 1 page <https://worldwide.espacenet.com/patent/search/family/047955997/publication/CN103006529A?q=CN103006529>.

* cited by examiner

*Primary Examiner* — Celeste A Roney

(57) ABSTRACT

A dentifrice composition and a method of making thereof are provided. The dentifrice composition includes an alginate, where the alginate is present in an amount from about 0.01 wt % to about 2 wt %, based on the total weight of the dentifrice composition; zinc compounds, wherein the zinc compounds include zinc oxide and zinc citrate trihydrate, wherein the zinc compounds are present in an amount from about 0.1 wt % to about 2 wt %, based on the total weight of the dentifrice composition; and an abrasive, wherein the abrasive includes calcium carbonate, wherein the abrasive is present in an amount from about 38 wt % to about 50 wt %, based on the total weight of the dentifrice composition.

19 Claims, No Drawings

ALGINATE DENTIFRICE COMPOSITIONS AND METHODS OF MAKING THEREOF

CROSS REFERENCE TO RELATED APPLICATIONS

This application is filed under 35 U.S.C. 371 claiming benefit of PCT Application No. PCT/CN2016/081558, filed on May 10, 2016, the contents of which are incorporated herein by reference.

BACKGROUND

The incorporation of zinc compounds, especially in the form of water soluble salts, into oral care products to provide antiplaque, anticalculus, and antibacterial effects is well-known. In addition, zinc can freshen breath by converting smelly volatile molecules into non-volatile ones. However, the use of zinc salts can have drawbacks. For example, they can give the oral care products an astringent taste. This unpleasant taste can inhibit their use in mass appeal products, and it can also impose some restrictions on the flavors that can be used. Using less soluble zinc salts may reduce the astringency of the oral care products, but it can also reduce the zinc's beneficial effects.

There is a desire, therefore, to develop improved oral care compositions that include zinc compounds with reduced astringency while maintaining the zinc compounds' beneficial effects.

BRIEF SUMMARY

Dentifrice compositions and methods for making the same are provided. In at least one specific embodiment, a dentifrice composition can include: an alginate, wherein the alginate is present in an amount from about 0.01 wt % to about 1.2 wt %, based on the total weight of the dentifrice composition; zinc compounds, where the zinc compounds can include zinc oxide and zinc citrate trihydrate, where the zinc compounds are present in an amount from about 0.1 wt % to about 2 wt %, based on the total weight of the dentifrice composition; and an abrasive, wherein the abrasive can include calcium carbonate, wherein the abrasive is present in an amount from about 38 wt % to about 50 wt %, based on the total weight of the dentifrice composition.

In another specific embodiment, a dentifrice composition can include: an alginate, where the alginate is present in an amount from about 0.01 wt % to about 1.2 wt %, based on the total weight of the dentifrice composition; zinc compounds, where the zinc compounds can include zinc oxide and zinc citrate trihydrate, where the zinc compounds are present in an amount from about 0.1 wt % to about 2 wt %, based on the total weight of the dentifrice composition; and an abrasive, where the abrasive can include silica, where the abrasive is present in an amount from about 18 wt % to about 26 wt %, based on the total weight of the dentifrice composition.

In another specific embodiment, a method of making a dentifrice composition can include: combining at least one humectant, at least one alginate, at least one additive, at least one sweeting agents, at least one anti-caries agent, at least one thickening agent, and at least one liquid medium to make a first mixture; mixing the first mixture for at least 20 minutes at a temperature of about 50° C. to about 58° C. Applying a vacuum of at least −0.070 MPa and mixing the first mixture for at least 5 minutes; combining at least one abrasive to the first mixture to make a second mixture; mixing the second mixture for at least 10 minutes; applying a vacuum of at least −0.08 MPa to the second mixture; combining at least one surfactant to the second mixture to make a third mixture; mixing the third mixture for at least 5 minutes at a temperature of at least 45° C.; releasing the vacuum over the third mixture; stopping mixing of third mixture; combining at least one zinc compound, at least one flavoring agent, and at least one additive to the third mixture to make a fourth mixture; mixing fourth mixture for at least 3 minutes; applying vacuum of at least −0.092 MPa to the fourth mixture; and mixing the fourth mixture for at least 10 minutes to make a dentifrice composition.

DETAILED DESCRIPTION

It has been found that alginate can be used to modulate and/or lessen the astringency of dentifrice or toothpaste compositions containing zinc compounds. The alginate can effectively modulate and/or lessen the astringent taste and mouthfeel during and/or after brushing, while still maintaining the efficacy of the at least one zinc compound' antibacterial, antiplaque, antitartar, and deodorant properties. For example, dentifrice compositions containing zinc citrate, zinc oxide and sodium alginate have significantly reduced astringent taste and mouthfeel compared to dentifrice compositions containing zinc citrate and zinc oxide, but no sodium alginate. Moreover, this reduction in astringent taste and mouthfeel for dentifrice composition containing zinc citrate, zinc oxide and sodium alginate can also be formulated using different abrasives, such as silica and calcium carbonate.

Zinc is believed to provide antibacterial efficacy by disrupting glucose metabolism and also interacting with the bacterial cell wall. This inhibits bacterial growth in the mouth. Without wanting to be bound by theory, it is believed that zinc can form a molecular complex with sodium alginate thereby modulating the astringent taste and mouthfeel of the dentifrice composition, yet without significantly affecting the zinc's ability to interact with the bacteria.

The dentifrice composition can include at least one alginate, at least one zinc compound, at least one liquid medium, at least one abrasive, at least one humectant, at least one thickening agent, at least one flavoring agent, at least one surfactant, at least one sweetening agent, at least one anti-caries agent, at least one additive, and mixtures thereof.

The total weight of the dentifrice composition can include the total weight of the at least one alginate salts, at least one zinc compound, at least one liquid medium, at least one abrasive, at least one humectant, at least one thickening agent, at least one flavoring agent, at least one surfactant, at least one sweetening agent, at least one anti-caries agent, and/or at least one additive.

Alginates

Alginate or alginic acid is a polymer derived from seaweeds and algae. The alginates can include alginates of varying molecular weights. The alginates can also include, but is not limited to, at least one of the salts forms of alginate, such as sodium alginate, potassium alginate, calcium alginate, or any mixture thereof. For example, sodium alginate is the sodium salt of alginate or alginic acid. Alginic acid and its salt forms are linear block copolymers with homopolymeric blocks of (1-4)-linked β-D-mannuronate residues and α-L-guluronate residues covalently bonded together in different blocks. The monomers can appear in homopolymeric blocks of consecutive β-D-mannuronate residues, consecutive α-L-guluronate residues or alternating β-D-mannuronate and α-L-guluronate residues.

The alginate can be present in the dentifrice composition from a low of about 0.001 wt %, about 0.1 wt %, about 1 wt %, or about 2 wt % to a high of about 6 wt %, about 9 wt %, about 12 wt %, or about 20 wt %, based on the total weight of the composition. For example, the dentifrice composition can include alginate from about 0.002 wt % to about 0.02 wt %, 0.01 wt % to about 1.2 wt %, about 0.2 wt % to about 1 wt %, about 0.4 wt % to about 1.5 wt %, about 0.6 wt % to about 0.8 wt %, about 0.6 wt % to about 1 wt %, about 0.9 wt % to about 1.7 wt %, about 3.7 wt % to about 5.9 wt %, about 4.7 wt % to about 12 wt %, about 11 wt % to about 23 wt %, or about 7 wt % to about 19 wt %, based on the total weight of the composition.

Zinc Compounds

The zinc compounds can include, but are not limited to: zinc chloride, zinc citrate, zinc oxide, zinc lactate, and any mixture thereof. For example, the zinc compounds can include a mixture of zinc oxide and zinc citrate. The dentifrice composition can include at least one zinc compound from a low of about 0.001 wt %, about 0.1 wt %, about 1 wt %, or about 2 wt % to a high of about 6 wt %, about 9 wt %, about 12 wt %, or about 20 wt %, based on the total weight of the composition. For example, the dentifrice composition can include at least one zinc compound from about 0.002 wt % to about 0.02 wt %, about 0.2 wt % to about 1 wt %, about 0.4 wt % to about 1.5 wt %, about 1.1 wt % to about 4.2 wt %, about 3.7 wt % to about 5.9 wt %, about 4.7 wt % to about 12 wt %, about 11 wt % to about 23 wt %, or about 7 wt % to about 19 wt %, based on the total weight of the composition. In another example, the dentifrice composition can include a first zinc compound (for example zinc oxide) in an amount of from about 0.4 wt % to about 2 wt %, about 0.5 to 1.5%, or 1 wt %, and a second zinc compound (for example zinc citrate) in an amount of from 0.1 to 1.5%, about 0.2 to 1%, or 0.5%.

If more than one zinc compound is present in the dentifrice composition, the zinc compounds can be mixed in any ratio to make the dentifrice composition. For example, if two zinc compounds are present in the dentifrice composition the mixing ratio of the two zinc compounds can be in a weight ratio of about 99:1, about 90:10, about 80:20, about 70:30, about 60:40, about 50:50, about 40:60, about 30:70, about 20:80, about 10:90, or about 1:99. In another example, the mixing ratio of the two zinc compounds can be in a weight ratio of about 0.05:1, about 1:1, about 1:2, about 2:3, about 3:7, or about 1:4. For example, the dentifrice composition can include a mixture of two zinc compounds in a ratio of 1:2. For example, the dentifrice composition can include a mixture of zinc citrate and zinc oxide in a ratio of 1:2.

Abrasives

The abrasives can include, but are not limited to: aluminum oxide; aluminum silicate; calcined alumina; bentonite; silica; zeolites; insoluble phosphates; calcium carbonate, such as natural calcium carbonate; and mixtures thereof. Insoluble phosphates can include, but are not limited to: dicalcium orthophosphate dihydrate, calcium pyrophosphate, calcium pyrophosphate, tricalcium phosphate, calcium polymetaphosphate, sodium polymetaphosphate, and mixtures thereof. Commercially available abrasives can be used in the dentifrice composition disclosed herein. Such commercially available abrasives can include, but is not limited to: ZEODENT® 105, 114, and 165, manufactured by J.M. Huber Corporation of Edison, N.J., and SYLODENT® 783, manufactured by W.R. Grace & Company of Columbia, Md.

The abrasive can be present in the dentifrice composition from a low of about 1 wt %, about 2 wt %, or about 4 wt %, to a high of about 20 wt %, about 25 wt %, or about 35 wt %, based on the total weight of the composition. For example, the abrasive can be present in the dentifrice composition from about 1 wt % to about 2 wt %, about 1.2 wt % to about 3 wt %, about 1.7 wt % to about 3.5 wt %, about 1.1 wt % to about 4.2 wt %, about 3.7 wt % to about 5.9 wt %, about 4.7 wt % to about 12 wt %, about 11 wt % to about 23 wt %, about 7 wt % to about 19 wt %, about 17 wt % to about 27 wt %, or about 20 wt % to about 35 wt %, based on the total weight of the composition.

Liquid Media

The liquid medium can include, but is not limited to: water, methanol, ethanol, ethyl acetate, acetone, isopropanol, and mixtures thereof. The liquid medium can be present in the dentifrice composition from a low of about 1 wt %, about 10 wt %, about 20 wt %, or about 40 wt % to a high of about 85 wt %, about 90 wt %, about 95 wt %, or about 99.5 wt %, based on the total weight of the composition. For example, the liquid medium can be present in the dentifrice composition from about 99 wt % or less, about 95 wt % or less, about 90 wt % or less, about 85 wt % or less, about 80 wt % or less, or about 75 wt % or less, based on the total weight of the composition. In another example, the liquid medium can be present in the dentifrice composition of about 15 wt % to about 25 wt %, about 20 wt % to about 30 wt %, about 20 wt % to about 59 wt %, about 25 wt % to about 35 wt %, about 47 wt % to about 80 wt %, about 73 wt % to about 93 wt %, about 80 wt % to about 99 wt %, about 90 wt % to about 98 wt %, or about 95 wt % to about 99 wt %, based on the total weight of the composition.

Humectants

The humectant can include, but is not limited to, sorbitol, glycerin, polyethylene glycol, or any mixture thereof. The humectant can be present in the dentifrice composition from a low of a low of about 1 wt %, about 5 wt %, about 7 wt %, or about 10 wt % to a high of about 50 wt %, about 60 wt %, about 72 wt %, or about 80 wt %, based on the total weight of the composition. For example, the humectant can be present in the dentifrice composition from about 1 wt % to about 12 wt %, about 20 wt % to about 40 wt %, about 39 wt % to about 55 wt %, about 41 wt % to about 62 wt %, about 47 wt % to about 81 wt %, about 55 wt % to about 85 wt %, about 60 wt % to about 75 wt %, 52 wt % to about 66 wt %, or about 61 wt % to about 79 wt %, based on the total weight of the composition.

Thickening Agents

The thickening agent can include, but is not limited to: carboxymethyl cellulose, such as carboxymethyl cellulose-tetramethylsilyl and carboxymethyl cellulose 2000S; tetrasodium pyrophosphate; xanthan gum; carrageenan gum and/or silica. A thickening agent can be present in the dentifrice composition from a low of about 0.1 wt %, about 1 wt %, about 2 wt %, or about 3 wt % to a high of about 6 wt %, about 9 wt %, about 12 wt %, or about 20 wt %, based on the total weight of the composition. For example, the thickening agent can be present in the dentifrice composition from about 0.01 wt % to about 0.1 wt %, about 0.1 wt % to about 1 wt %, about 1 wt % to about 4 wt %, about 2 wt % to about 6 wt %, about 4 wt % to about 8 wt %, about 5 wt % to about 10 wt %, about 7 wt % to about 12 wt %, about 11 wt % to about 18 wt %, about 13 wt % to about 17 wt %, or about 8 wt % to about 20 wt %, based on the total weight of the composition. Commercially available thickening agents can be used in the dentifrice composition disclosed herein.

Flavoring Agents

The flavoring agent or dentifrice flavor can include, but is not limited to: vanillin, sage, marjoram, parsley oil, spearmint oil, cinnamon, wintergreen oil (methylsalicylate), peppermint oil; clove oil; bay oil; anise oil; citrus oils; fruit oils and essences, such as those derived from lemon, orange, lime, grapefruit, apricot, banana, grape, apple, strawberry, cherry, pineapple, and the like; bean- and nut-derived flavors, such as coffee, cocoa, cola, peanut, almond, and the like; sassafras; clove; sage; eucalyptus; marjoram; menthol; carvone; anethole; salt white flavor; cyclamates; acesulfane-K; thaumatin; neohisperidin dihydrochalcone; D-tryptophan, ammoniated glycyrrhizin; and mixtures thereof. Also encompassed within flavoring agents herein are ingredients that provide fragrance and/or other sensory effects in the mouth, such as cooling or warming effects. Such agents can include, but is not limited to: menthol; menthyl acetate; menthyl lactate; camphor; eucalyptus oil; eucalyptol; anethole; eugenol; cassia; oxanone; α-irisone; propenyl guaiethol; thymol; linalool; benzaldehyde; cinnamaldehyde; N-ethyl-p-menthan-3-carboxamine; N,2,3-trimethyl-2-isopropylbutanamide, 3-(1-menthoxy)-propane-1,2-diol; cinnamaldehyde glycerol acetal, menthone glycerol acetal (MGA) and the like. Commercially available flavoring agents can be used in the dentifrice composition disclosed herein.

The flavoring agent can be present in the dentifrice composition from a low of about 0.01 wt %, about 0.1 wt %, or about 1 wt %, to a high of about 4 wt %, about 5 wt %, or about 6 wt %, based on the total weight of the composition. For example, the flavoring agent can be present in the dentifrice composition from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, or about 1.7 wt % to about 5.9 wt %, based on the total weight of the composition.

Surfactants

The surfactant can be anionic, cationic, zwitterionic, or nonionic surfactants, and mixtures thereof. Suitable anionic surfactant include without limitation, water-soluble salts of $C_{8-20}$ alkyl sulfates, sulfonated monoglycerides of $C_{8-20}$ fatty acids, sarcosinates, taurates and the like. Illustrative examples of these and other classes can include sodium lauryl sulfate ("SLS"), sodium coconut monoglyceride sulfonate, sodium lauryl sarcosinate, sodium lauryl isethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate.

The surfactant can be present in the dentifrice composition from a low of about 1 wt %, about 2 wt %, or about 4 wt %, to a high of about 20 wt %, about 25 wt %, or about 35 wt %, based on the total weight of the composition. For example, the surfactant can be present in the dentifrice composition from about 1 wt % to about 2 wt %, about 1.2 wt % to about 3 wt %, about 1.7 wt % to about 3.5 wt %, about 1.1 wt % to about 4.2 wt %, about 3.7 wt % to about 5.9 wt %, about 4.7 wt % to about 12 wt %, about 11 wt % to about 23 wt %, about 7 wt % to about 19 wt %, about 17 wt % to about 27 wt %, or about 20 wt % to about 35 wt %, based on the total weight of the composition.

Sweetening Agents

The sweetening agent can include, but is not limited to: saccharin, xylitol, perillartien, sucrose, glucose, sucralose, dextrose, levulose, lactose, thaumatin, neohisperidin dihydrochalcone, mannitol, sorbitol, fructose, maltose, xylitol, thaumatin, aspartame, dihydrochalcones, xylitol, acesulfame, cyclamate salts, and mixtures thereof. The sweetening agent can be present in the dentifrice composition from a low of about 0.01 wt %, about 0.1 wt %, or about 1 wt %, to a high of about 4 wt %, about 5 wt %, or about 6 wt %, based on the total weight of the composition. For example, the sweetening agent can be present in the dentifrice composition from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, or about 1.7 wt % to about 5.9 wt %, based on the total weight of the composition.

Anti-Caries Agents

The anti-caries agent can include, but is not limited to, at least one fluoride compound. The fluoride compound can include, but is not limited to: sodium fluoride, potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, amine fluorides, and mixtures thereof.

The anti-caries agent can be present in the dentifrice composition a low of about 0.1 wt %, about 1 wt %, about 2 wt %, or about 3 wt % to a high of about 6 wt %, about 9 wt %, about 12 wt %, or about 20 wt %, based on the total weight of the composition. For example, the anti-caries agent can be present in the dentifrice composition from about 0.01 wt % to about 0.1 wt %, about 0.1 wt % to about 1 wt %, about 1 wt % to about 4 wt %, about 2 wt % to about 6 wt %, about 4 wt % to about 8 wt %, about 5 wt % to about 10 wt %, about 7 wt % to about 12 wt %, about 11 wt % to about 18 wt %, about 13 wt % to about 17 wt %, or about 8 wt % to about 20 wt %, based on the total weight of the composition.

In another aspect, the fluoride compound can dissociate to provide fluoride ions in a concentration from a low of about 5,000 ppm, about 7,000 ppm, about 9,000 ppm, or about 10,000 ppm to a high of about 20,000 ppm, about 30,000 ppm, 40,000, or about 50,000 ppm. For example, the fluoride compound can dissociate to provide fluoride ions in a concentration from about 5,000 ppm to about 7,000 ppm, about 6,000 ppm to about 12,000 ppm, about 11,000 ppm to about 21,000 ppm, about 19,000 ppm to about 27,000 ppm, about 26,000 ppm to about 37,000 ppm, about 25,000 ppm to about 37,000 ppm, or about 28,000 ppm to about 50,000 ppm. In order to provide such a concentration in the desired ppm range, the exact weight percentage of the at least one fluoride compounds in the dentifrice composition can vary widely, depending upon the stoichiometric ratio of the fluoride within the compound.

Additives

The additive can include, but is not limited to: at least one coloring agent, at least one preservative, at least one tartar control agent, at least one base; at least one acid, at least one antimicrobial agent, at least one teeth whitener, at least one saliva stimulating agent, at least one anti-sensitivity agent, at least one antioxidant, and mixtures thereof.

Coloring Agents

The coloring agent can include, but is not limited to: pigments, dyes, lakes and agents imparting a particular luster or reflectivity, such as pearling agents. The coloring agent can include, but is not limited to: talc; mica; magnesium carbonate; calcium carbonate; magnesium silicate; magnesium aluminum silicate; silica; Timiron MP-149, titanium dioxide; iron oxides; ferric ammonium ferrocyanide, manganese violet; ultramarine; titaniated mica; bismuth oxychloride; and mixtures thereof. Commercially available coloring agents can be used in the dentifrice composition disclosed herein.

The coloring agent can be present in the dentifrice composition from a low of about 0.0001 wt %, about 0.001 wt %, 0.01 wt %, or about 0.1 wt %, to a high of about 3 wt %, about 4 wt %, or about 4 wt %, based on the total weight of the composition. For example, the coloring agent can be present in the dentifrice composition from about 0.0001 wt % to about 0.01 wt %, about 0.001 wt % to about 0.1 wt %, about 0.1 wt % to about 0.9 wt %, about 0.8 wt % to about 1.2 wt %, about 0.7 wt % to about 1.9 wt %, about 1.7 wt % to about 2.9 wt %, about 1.1 wt % to about 3.9 wt %, about 2.7 wt % to about 3.9 wt %, about 1.7 wt % to about 4.9 wt %, based on the total weight of the composition.

Tartar Control Agents

The tartar control agent can include: phosphates and polyphosphates (for example pyrophosphates); polyaminopropanesulfonic acid (AMPS); polyolefin sulfonates; polyolefin phosphates; diphosphonates, such as azacycloalkane-2,2-diphosphonates (e.g., azacycloheptane-2,2-diphosphonic acid); N-methyl azacyclopentane-2,3-diphosphonic acid; ethane-1-hydroxy-1,1-diphosphonic acid (EHDP), and ethane-1-amino-1,1-diphosphonate, phosphonoalkane carboxylic acids, and the like. Useful inorganic phosphate and polyphosphate salts include monobasic, dibasic and tribasic sodium phosphates, such as sodium tripolyphosphate, tetrapolyphosphate, mono-, di-, tri- and tetrasodium pyrophosphates, sodium trimetaphosphate, sodium hexametaphosphate, and mixtures thereof.

The tartar control agent can be present in the dentifrice composition from a low of about 0.01 wt %, about 0.1 wt %, or about 1 wt %, to a high of about 4 wt %, about 5 wt %, or about 6 wt %, based on the total weight of the composition. For example, the tartar control agent can be present in the dentifrice composition from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, or about 1.7 wt % to about 5.9 wt %, based on the total weight of the composition.

Preservatives

The preservative can include, but is not limited to: betaine; benzoates, such as sodium benzoate, potassium benzoate, methyl paraben, and ethyl paraben; dichlorinated phenols; and mixtures thereof. The preservative can be present in the dentifrice composition from a low of about 0.01 wt %, about 0.1 wt %, or about 1 wt %, to a high of about 4 wt %, about 5 wt %, or about 6 wt %, based on the total weight of the composition. For example, the preservative can be present in the dentifrice composition from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, or about 1.7 wt % to about 5.9 wt %, based on the total weight of the composition.

Anti-Microbial Agents

The anti-microbial agent can include, but is not limited: benzoic acid, potassium benzoate, boric acid, betanaphthol, chlorothymol, thymol, anethole, eucalyptol, carvacrol, menthol, phenol, amylphenol, hexylphenol, heptylphenol, octylphenol, hexylresorcinol, laurylpyridinium chloride, myristylpyridinium chloride, cetlpyridinium fluoride, cetylpyridinium chloride, cetylpyridinium bromide, triclosan, chlorhexidine; triclosan; quaternary ammonium compounds, such as benzalkonium chloride; parabens, such as methylparaben or propylparaben; and mixtures thereof.

The anti-microbial agent can be present in the dentifrice composition from a low of about 0.01 wt %, about 0.1 wt %, or about 1 wt %, to a high of about 4 wt %, about 5 wt %, or about 6 wt %, based on the total weight of the composition. For example, the anti-microbial agent can be present in the dentifrice composition from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, or about 1.7 wt % to about 5.9 wt %, based on the total weight of the composition.

Anti-Sensitivity Agents

The anti-sensitivity agent can include, but is not limited: potassium salts, such as potassium nitrate, potassium bicarbonate, potassium chloride, potassium citrate, and potassium oxalate; capsaicin; eugenol; strontium salts; zinc salts; chloride salts; and mixtures thereof. The dentifrice composition may treat hyper-sensitivity by blocking dentin tubules.

The anti-sensitivity agent can be present in the dentifrice composition from a low of about 0.01 wt %, about 0.1 wt %, or about 1 wt %, to a high of about 4 wt %, about 5 wt %, or about 6 wt %, based on the total weight of the composition. For example, the anti-sensitivity agent can be present in the dentifrice composition from about 0.01 wt % to about 0.1 wt %, about 0.1 wt % to about 1 wt %, about 1 wt % to about 4 wt %, about 2 wt % to about 6 wt %, about 4 wt % to about 8 wt %, about 5 wt % to about 10 wt %, about 7 wt % to about 12 wt %, about 11 wt % to about 18 wt %, about 13 wt % to about 17 wt %, or about 8 wt % to about 20 wt %, based on the total weight of the composition.

Tooth Whitening Agents

The tooth whitening agent can include, but is not limited to: peroxides, such as hydroperoxides, hydrogen peroxide, lithium peroxide, potassium peroxide, sodium peroxide, magnesium peroxide, calcium peroxide, barium peroxide, peroxy acids; metal chlorites, such as calcium chlorite, barium chlorite, magnesium chlorite, lithium chlorite, sodium chlorite, and potassium chlorite; persulfates; sodium perborate; and mixtures thereof.

The tooth whitening agent can be present in the dentifrice composition from a low of about 0.01 wt %, about 0.1 wt %, or about 1 wt %, to a high of about 4 wt %, about 5 wt %, or about 6 wt %, based on the total weight of the composition. For example, the tooth whitening agent can be present in the dentifrice composition from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, or about 1.7 wt % to about 5.9 wt %, based on the total weight of the composition.

Bicarbonate Salts

The bicarbonate salt can impart a "clean feel" to teeth and gums due to effervescence and release of carbon dioxide. The bicarbonate salt can include, but is not limited to: alkali metal bicarbonates, such as sodium and potassium bicarbonates, ammonium bicarbonate and the like. The bicarbonate salt can be present in the dentifrice composition from a low of about 0.01 wt %, about 0.1 wt %, or about 1 wt %, to a high of about 4 wt %, about 5 wt %, or about 6 wt %, based on the total weight of the composition. For example, the bicarbonate salt can be present in the dentifrice composition from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, or about 1.7 wt % to about 5.9 wt %, based on the total weight of the composition.

Antioxidants

The antioxidant can include, but is not limited to: butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof. The antioxidant can be present in the dentifrice composition from a low of about 0.1 wt %, about 1 wt %, about 2 wt %, or about 3 wt % to a high of about 6 wt %, about 9 wt %, about 12 wt %, or about 20 wt %, based on the total weight of the composition. For example, the antioxidant can be present in the dentifrice composition from about 0.01 wt % to about 0.1 wt %, about 0.1 wt % to about 1 wt %, about 1 wt % to about 4 wt %, about 2 wt % to about 6 wt %, about 4 wt % to about 8 wt %, about 5 wt % to about 10 wt %, about 7 wt % to about 12 wt %, about 11 wt % to about 18 wt %, about 13 wt % to about 17 wt %, or about 8 wt % to about 20 wt %, based on the total weight of the composition.

Acids and Bases

Acids and/or bases can be used to adjust the pH and/or buffer the dentifrice composition. The acids can include, but is not limited to: sodium carbonate, sodium bicarbonate, sodium dihydrogen phosphate, sodium hydrogen phosphate, trisodium phosphate, sodium hydroxide, sodium carbonate, citric acid, sodium citrate, and mixtures thereof. The bases can include, but is not limited to: sodium hydroxide, potassium hydroxide, and mixtures thereof. The dentifrice composition can have a pH from a low of 4.0 to a high of about pH 9.0. For example, the dentifrice composition can have pH from about 4.0 to about 5.0, about 4.5 to about 6.0, about 5.5 to about 6.5, about 6.0 to about 7.0, about 6.5 to about 8.0, or about 7.5 to about 9.0.

The acids and/or bases can be present in the dentifrice composition from a low of about 0.01 wt %, about 0.1 wt %, or about 1 wt %, to a high of about 4 wt %, about 5 wt %, or about 6 wt %, based on the total weight of the composition. For example, the acids and/or bases can be present in the dentifrice composition from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, or about 1.7 wt % to about 5.9 wt %, based on the total weight of the composition.

The dentifrice composition can be a solid, liquid, dispersion, emulsion, suspension, slurry, gel or any mixture thereof. The viscosity of the dentifrice compositions can vary widely. For example, the viscosity of the dentifrice composition can be from a low of about 1 centipoise ("cP"), about 1,000 cP, about 1,250 cP, about 20,000 cP, or about 30,000 cP to a high of about 500,000 cP, about 700,000 cP, about 800,000 cP, or about 900,000 cP at a temperature of about 25° C. For example, dentifrice composition can have a viscosity from about 1,500 cP to about 12,500 cP, about 12,000 cP to about 75,000 cP, about 25,000 cP to about 125,000 cP, about 160,000 cP to about 460,000 cP, about 55,000 cP to about 400,000 cP, about 350,000 cP to about 550,000 cP, about 150,000 cP to about 650,000 cP, or about 345,000 cP to about 700,000 cP at a temperature of about 25° C. In another example, the dentifrice composition can have a viscosity from about 245,000 cP to about 500,000 cP, about 445,000 cP to about 650,000 cP, or about 600,000 cP to about 900,000 cP at a temperature of about 25° C. The viscosity can be measured using a viscometer.

Methods of Making Zinc Compounds and Sodium Alginate Dentifrice Compositions

A method for making zinc compounds and sodium alginate dentifrice compositions that use natural calcium carbonate as the abrasive can include, but is not limited to: combining at least one humectant, at least one alginate, at least one additive, at least one sweetening agent, at least one anti-caries agent, at least one thickening agent, and at least one liquid medium to make a first mixture; mixing the first mixture for at least 20 minutes at a temperature of about 50° C. to about 58° C. The first mixture can be transferred from the reaction vessel into a mixer, such as a Li-yuan mixer. Applying a vacuum of at least −0.070 MPa and mixing the first mixture for at least 5 minutes in the vacuum; combining at least one abrasive to the first mixture to make a second mixture; mixing the second mixture for at least 10 minutes; applying a vacuum of at least −0.080 MPa to the second mixture; combining at least one surfactant to the second mixture to make a third mixture; mixing the third mixture for at least 5 minutes at a temperature of at least 45° C.; releasing the vacuum over third mixture; stopping the mixing of third mixture; combining at least one zinc compound, at least one flavoring agent, and at least one additive into the third mixture to make a fourth mixture; mixing the fourth mixture for at least 3 minutes; applying vacuum of at least −0.092 MPa to the fourth mixture; and mixing the fourth mixture for at least 10 minutes before releasing the vacuum to make a dentifrice composition.

A method for making zinc compounds and sodium alginate dentifrice compositions that use silica as the abrasive can include, but is not limited to: combining at least one humectant, at least one alginate, at least one thickening agent, at least one anti-caries agent, at least one abrasive, at least one sweetening agent, at least one liquid medium to a reaction vessel to make a first mixture; increasing the temperature of the first mixture to at least 45° C. and mixing for at least 15 minutes. The first mixture can be transferred from the reaction vessel into a mixer, such as a Li-yuan mixer. Applying a vacuum over the first mixture of at least −0.07 MPa and mixing for at least 2 minutes; increasing the vacuum over the first mixture to at least −0.08 MPa and mixing for at least 10 minutes; reducing the temperature of the first mixture to less than 45° C. and releasing the vacuum; combining at least one flavoring agent, at least one additive, at least one abrasive, at least one surfactant, and at least one zinc compound to make a second mixture; mixing the second mixture for at least 3 minutes; applying a vacuum of at least −0.08 MPa over the second mixture and mixing for at least 15 minutes to make a dentifrice composition.

Further disclosed herein are methods of using the dentifrice composition. The dentifrice composition can be applied to the surface of a tooth to clean and/or inhibit dental caries. The dentifrice composition can be applied to a tooth by any means. An applicator, such as a brush or a dental tray, can be used to apply the composition. For example, the dentifrice composition can be applied by contacting a brush with the composition and then using the brush to contact the composition to the surface of a tooth. Or in other words, the dentifrice composition can be applied by a user brushing his or her teeth using a toothbrush.

EXAMPLES

In order to provide a better understanding of the foregoing discussion, the following non-limiting examples are offered. Although the examples can be directed to specific embodiments, they are not to be viewed as limiting the invention in any specific respect.

Table 1 shows example dentifrice compositions containing sodium alginate, the zinc compounds, zinc citrate trihydrate and zinc oxide, and natural calcium carbonate as the abrasive.

TABLE 1

Zinc Compounds and Sodium Alginate Dentifrice Composition with Natural Calcium Carbonate

| Ingredients | Ex. 1 | Ex. 2 | Ex. 3 |
|---|---|---|---|
| Humectant | 21.00 | 21.00 | 21.00 |
| Sweetener | 0.25 | 0.25 | 0.25 |
| Monosodium Fluorophosphate | 1.10 | 1.10 | 1.10 |
| Thickening Agent | 1.00 | 1.00 | 1.00 |
| Sodium Alginate | 0.06 | 0.08 | 0.10 |
| Sodium Bicarbonate | 0.20 | 0.20 | 0.20 |
| Sodium Carbonate | 0.80 | 0.80 | 0.80 |

TABLE 1-continued

Zinc Compounds and Sodium Alginate Dentifrice Composition with Natural Calcium Carbonate

| Ingredients | Ex. 1 | Ex. 2 | Ex. 3 |
|---|---|---|---|
| Purified Water | 23.08 | 23.06 | 23.04 |
| Natural Calcium Carbonate | 42.00 | 42.00 | 42.00 |
| Silica Abrasive | 2.00 | 2.00 | 2.00 |
| Benzyl Alcohol | 0.30 | 0.30 | 0.30 |
| 35% Liquid SLS | 5.71 | 5.71 | 5.71 |
| Dentifrice Flavor | 1.00 | 1.00 | 1.00 |
| Zinc Citrate Trihydrate | 0.50 | 0.50 | 0.50 |
| ZnO | 1.00 | 1.00 | 1.00 |
| Total | 100.00 | 100.00 | 100.00 |

The dentifrice compositions were made by combining a formula amount of humectant, monosodium fluorophosphate, sweetener, sodium bicarbonate, sodium carbonate, thickening agent, and sodium alginate into a reaction vessel and stirring for 5 minutes at room temperature to fully incorporate the ingredients. A formula weight of water was added to the reaction vessel to make a first mixture. The first mixture was stirred for 20 minutes at a temperature of between 50° C. and 58° C. The first mixture was transferred from the reaction vessel into a Li-yuan mixer. The first mixture was put under a vacuum of −0.070 MPa. The homogenizer and mixer on the Li-yuan mixer was set to 10/1800 rotations per minute (rpm). The first mixture was stirred for 5 minutes. The viscosity of the first mixture was periodically measured by a viscometer. A vacuum of −0.070 MPa was applied to the first mixture. A formula amount of abrasive (natural calcium carbonate and silica) was added to the first mixture to make a second mixture. The second mixture was mixed for 10 minutes. A vacuum of −0.080 MPa was applied to the second mixture. A formula amount of 35 wt % liquid sodium lauryl sulfate was combined with the second mixture to make a third mixture. The third mixture was mixed for 5 minutes at a temperature of 46° C. The vacuum over the third mixture was released and mixing stopped. A formula weight of dentifrice flavor, benzoic acid, zinc citrate trihydrate, and zinc oxide was added to the third mixture to make a fourth mixture. The fourth mixture was mixed for 3 minutes without vacuum. A vacuum of −0.092 MPa was applied to the fourth mixture and it was mixed for 10 minutes to make the dentifrice compositions.

Table 2 shows example dentifrice compositions containing sodium alginate, the zinc compounds, zinc citrate trihydrate and zinc oxide, and abrasive.

TABLE 2

Zinc Compounds and Sodium Alginate Dentifrice Composition with Silica

| Ingredients | Ex. 4 | Ex. 5 | Ex. 6 |
|---|---|---|---|
| Humectant, 70% Solution | 50.00 | 50.00 | 50.00 |
| 99.0-101% Glycerin USP (Vegetable) | 2.00 | 2.00 | 2.00 |
| Silica Abrasive 1 | 10.00 | 10.00 | 10.00 |
| Silica Abrasive 2 | 6.00 | 6.00 | 6.00 |
| Silica Abrasive 3 | 5.00 | 5.00 | 5.00 |
| Thickening Agents | 1.60 | 1.60 | 1.60 |
| Sodium Alginate | 0.06 | 0.08 | 0.10 |
| Sodium Fluoride | 0.32 | 0.32 | 0.32 |
| 35 wt % Liquid Sodium Lauryl Sulfate | 5.71 | 5.71 | 5.71 |
| Betaine | 1.25 | 1.25 | 1.25 |
| Sweetener | 0.35 | 0.35 | 0.35 |
| Dentifrice Flavor | 1.20 | 1.20 | 1.20 |

TABLE 2-continued

Zinc Compounds and Sodium Alginate Dentifrice Composition with Silica

| Ingredients | Ex. 4 | Ex. 5 | Ex. 6 |
|---|---|---|---|
| Colorants | 0.70 | 0.70 | 0.70 |
| Zinc Citrate Trihydrate | 0.50 | 0.50 | 0.50 |
| Zinc Oxide | 1.00 | 1.00 | 1.00 |
| Benzyl Alcohol | 0.10 | 0.10 | 0.10 |
| Demineralized Water | 14.21 | 14.19 | 14.17 |
| Total | 100.00 | 100.00 | 100.00 |

The dentifrice compositions were made by combining a formula amount of sorbitol, glycerin, thickening agents, sodium alginate, sodium fluoride, sweetener and colorants into a reaction vessel and stirring to incorporate the ingredients. A formula amount of water was added to the reaction vessel to make a first mixture. The temperature of the first mixture was increased to 45° C. and it was mixed for 15 minutes. The first mixture was transferred from the reaction vessel into a Li-yuan mixer. The first mixture was placed under vacuum of −0.07 MPa. The homogenizer and mixer on the Li-yuan mixer was set to 70/1800 rotations per minute (rpm). The first mixture was mixed for 2 minutes. The vacuum over the first mixture was increased to −0.08 MPa. The first mixture was mixed for 10 minutes. The temperature of the first mixture was reduced to less than 45° C., and the vacuum released. A formula amount of dentifrice flavor, benzyl acid, additional colorant, 35 wt % liquid sodium lauryl sulfate, zinc citrate trihydrate, and zinc oxide were combined with the first mixture to make a second mixture. The second mixture was mixed for 3 minutes. The second mixture was placed under vacuum of greater than −0.08 MPa, and mixed for 15 minutes to make the dentifrice composition.

Astringency Comparison Test

An astringency comparison test was used to compare the astringency of a natural calcium carbonate-based dentifrice composition containing sodium alginate and a dentifrice composition without sodium alginate. Table 3 shows the inventive dentifrice composition (Ex. 7) containing sodium alginate, the zinc compounds zinc citrate trihydrate and zinc oxide, and natural calcium carbonate as the abrasive, and the control dentifrice composition (C1) containing the zinc compounds zinc citrate trihydrate and zinc oxide, and natural calcium carbonate as the abrasive.

TABLE 3

Compositions for Astringency Comparison

| Ingredients | C1 | Ex. 7 |
|---|---|---|
| Humectant | 21.00 | 21.00 |
| Sweetener | 0.25 | 0.25 |
| Monosodium Fluorophosphate | 1.10 | 1.10 |
| Thickening Agent | 1.00 | 1.00 |
| Sodium Alginate | — | 0.06 |
| Sodium Bicarbonate | 0.20 | 0.20 |
| Sodium Carbonate | 0.80 | 0.80 |
| Purified Water | 22.14 | 23.08 |
| Natural Calcium Carbonate | 42.00 | 42.00 |
| Silica Abrasive | 2.00 | 2.00 |
| Benzyl Alcohol | 0.30 | 0.30 |
| 35% Liquid SLS | 5.71 | 5.71 |
| Dentifrice Flavor | 1.00 | 1.00 |
| Magnesium Aluminum Silicate | 1.00 | — |

TABLE 3-continued

Compositions for Astringency Comparison

| Ingredients | C1 | Ex. 7 |
|---|---|---|
| Zinc Citrate Trihydrate | 0.50 | 0.50 |
| Zinc Oxide | 1.00 | 1.00 |
| Total | 100.00 | 100.00 |

Table 4 shows the results of the astringency comparison test.

TABLE 4

Astringency Comparison Test of C1 and Ex. 7

| | A: C1 More Astringent | B: Ex. 7 More Astringent | NA: Same Intensity or Neither are Astringent |
|---|---|---|---|
| Astringency Comparison | 50% | 25% | 25% |

A/B Significant difference at 90% Confidence Limit (1-tailed)

Twenty panelists participated in the astringency comparison test. The test showed that 50% of the panelists rated C1 more astringent than Ex. 7, while only 25% panelists rated Ex. 7 as more stringent than C1. In other words, the composition with sodium alginate was significantly less astringent than that without sodium alginate.

An astringency comparison test was used to compare the astringency of a silica-based dentifrice composition containing sodium alginate and a dentifrice composition without sodium alginate. Table 5 shows the inventive dentifrice composition (Ex. 9) containing sodium alginate, the zinc compounds zinc citrate trihydrate and zinc oxide, and silica as the abrasive, and the control dentifrice composition (C1) containing the zinc compounds, zinc citrate trihydrate and zinc oxide, and silica as the abrasive.

TABLE 5

Compositions for Astringency Comparison

| Ingredients | C2 | Ex. 9 |
|---|---|---|
| Non-Crystallizing Sorbitol, 70% Solution | 50.00 | 50.00 |
| 99.0-101% Glycerin USP (Vegetable) | 2.00 | 2.00 |
| Silica Abrasive 1 | 10.00 | 10.00 |
| Silica Abrasive 2 | 6.00 | 6.00 |
| Silica Abrasive 3 | 5.00 | 5.00 |
| Thickening Agents | 1.60 | 1.60 |
| Sodium Alginate | — | 0.10 |
| Sodium Fluoride | 0.32 | 0.32 |
| 35% Sodium Lauryl Sulfate | 5.71 | 5.71 |
| Betaine | 1.25 | 1.25 |
| Sweetener | 0.35 | 0.35 |
| Dentifrice Flavor | 1.20 | 1.20 |
| Colorant | 0.70 | 0.70 |
| Zinc Oxide | 1.00 | 1.00 |
| Zinc Citrate Trihydrate | 0.50 | 0.50 |
| Benzyl Alcohol | 0.10 | 0.10 |
| Demineralized Water | 14.27 | 14.17 |
| Total | 100.00 | 100.00 |

Table 6 shows the results of the astringency comparison test.

TABLE 6

Astringency Comparison Test of C2 and Ex. 9

| | A: C2 More Astringent | B: Ex. 9 More Astringent | NA: Same Intensity or Neither are Astringent |
|---|---|---|---|
| Astringency Comparison | 55% | 15% | 30% |

A/B Significant difference at 90% Confidence Limit (1-tailed)

Twenty panelists participated in the astringency comparison test. The test showed that 55% of the panelists rated C2 more astringent than Ex. 9, while only 15% panelists rated Ex. 9 as more stringent than C2. In other words, the composition with sodium alginate was significantly less astringent than that without sodium alginate.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility. It is therefore intended by the appended claims to cover any and all such applications, modifications and embodiments within the scope of the present invention.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. It should also be appreciated that the numerical limits may be the values from the examples. Certain lower limits, upper limits and ranges appear in at least one claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

What is claimed is:

1. A toothpaste comprising:
   an alginate, wherein the alginate is present in an amount from about 0.01 wt % to about 1.2 wt %, based on the total weight of the toothpaste;
   zinc compounds, wherein the zinc compounds comprise zinc oxide and zinc citrate trihydrate, wherein the zinc compounds are present in an amount from about 0.1 wt % to about 2 wt %, based on the total weight of the toothpaste, wherein the zinc citrate trihydrate and zinc oxide in a weight ratio of about 1:2; and
   an abrasive, wherein the abrasive comprises calcium carbonate, wherein the abrasive is present in an amount from about 2 wt % to about 50 wt %, based on the total weight of the toothpaste,
   wherein the toothpaste does not contain a polyphosphate and wherein the toothpaste is free of nonionic surfactants.

2. The toothpaste as in claim 1, wherein the alginate is present in an amount from about 0.06 wt % to about 1 wt %, based on the total weight of the toothpaste;
   wherein the zinc compounds are present in an amount from about 1.4 wt % to about 1.6 wt %, based on the total weight of the toothpaste; and
   wherein the abrasive is present in an amount from about 42 wt % to about 46 wt %, based on the total weight of the toothpaste.

3. The toothpaste as in claim 1, further comprising a liquid medium, wherein the liquid medium comprises water, wherein the liquid medium is present in an amount from about 24 wt % to about 26 wt %, based on the total weight of the toothpaste;
   a humectant, wherein the humectant comprises sorbitol, wherein the humectant is present in an amount from about 18 wt % to about 22 wt %, based on the total weight of the toothpaste;
   thickening agents, wherein the thickening agents comprise carboxymethyl cellulose; wherein the thickening agents are present in an amount from about 0.8 wt % to about 2 wt %, based on the total weight of the toothpaste;
   a flavoring agent, wherein the flavoring agent is present in an amount from about 0.8 wt % to about 1.2 wt %, based on the total weight of the toothpaste;
   a surfactant, wherein the surfactant comprises sodium lauryl sulfate, wherein the surfactant is present in an amount from about 1.6 wt % to about 2.2 wt %, based on the total weight of the toothpaste;
   a sweetening agent, wherein the sweetening agent comprises sodium saccharin, wherein the sweetening agent is present in an amount from about 0.2 wt % to about 1 wt %, based on the total weight of the toothpaste;
   an anti-caries agent, wherein the anti-caries agent comprises sodium monofluorophosphate, wherein the anti-caries agent is present in an amount from about 0.8 wt % to about 1.4 wt %, based on the total weight of the toothpaste; and
   additives, wherein the additives comprise sodium carbonate, sodium bicarbonate, and benzyl alcohol, wherein the additives are present in an amount from about 0.5 wt % to about 5 wt %, based on the total weight of the toothpaste.

4. The toothpaste as in claim 1, further comprising abrasives selected from the group consisting of: aluminum oxide; aluminum silicate; calcined alumina; bentonite, silica, zeolites, and calcium carbonate.

5. A toothpaste comprising:
   an alginate, wherein the alginate is present in an amount from about 0.01 wt % to about 1.2 wt %, based on the total weight of the toothpaste;
   zinc compounds, wherein the zinc compounds comprise zinc oxide and zinc citrate trihydrate, the zinc citrate trihydrate and the zinc oxide being present in a weight ratio of about 1:1 to about 1:4; wherein the zinc compounds are present in an amount from about 0.1 wt % to about 2 wt %, based on the total weight of the toothpaste;
   abrasives, wherein the abrasives comprise silica, wherein the abrasives are present in an amount from about 18 wt % to about 26 wt %, based on the total weight of the toothpaste, wherein the toothpaste does not contain a polyphosphate and is free of nonionic surfactants.

6. The toothpaste as in claim 5, wherein the alginate is present in an amount from about 0.06 wt % to about 1 wt %, based on the total weight of the toothpaste;
wherein the zinc compounds are present in an amount from about 1.4 wt % to about 1.6 wt %, based on the total weight of the toothpaste; and
wherein the abrasives are present in an amount from about 20 wt % to about 23 wt %, based on the total weight of the toothpaste.

7. The toothpaste as in claim 5, further comprising a liquid medium, wherein the liquid medium comprises water, wherein the liquid medium is present in an amount from about 28 wt % to about 36 wt %, based on the total weight of the toothpaste;
humectants, wherein the humectants comprise sorbitol and glycerin, wherein the humectants are present in an amount from about 32 wt % to about 42 wt %, based on the total weight of the toothpaste;
thickening agents, wherein the thickening agents comprise carboxymethyl cellulose and xanthan gum, wherein the thickening agents are present in an amount from about 1 wt % to about 2 wt %, based on the total weight of the toothpaste;
a flavoring agent, wherein the flavoring agent is present in an amount from about 0.8 wt % to about 1.5 wt %, based on the total weight of the toothpaste;
a surfactant, wherein the surfactant comprises sodium lauryl sulfate, wherein the surfactant is present in an amount from about 1.6 wt % to about 2.4 wt %, based on the total weight of the toothpaste;
a sweetening agent, wherein the sweetening agent comprises sodium saccharin, wherein the sweetening agent is present in an amount from about 0.25 wt % to about 0.45 wt %, based on the total weight of the toothpaste;
an anti-caries agent, wherein the anti-caries agent comprises sodium fluoride, wherein the anti-caries agent is present in an amount from about 0.25 wt % to about 0.45 wt %, based on the total weight of the toothpaste; and
additives, wherein the additives comprise betaine and benzyl alcohol, wherein the additives are present in an amount from about 0.8 wt % to about 1.5 wt %, based on the total weight of the toothpaste.

8. The toothpaste as in claim 7, wherein the additives further comprise a coloring agent, a preservative, and a base.

9. The toothpaste as in claim 6, wherein the zinc citrate trihydrate and zinc oxide are in a weight ratio of about 1:2.

10. A method of making a dentifrice composition according to claim 5, the method comprising:
combining at least one humectant, at least one alginate, at least one additive, at least one sweetening agent, at least one anti-caries agent, at least one thickening agent, and at least one liquid medium to make a first mixture;
mixing the first mixture for at least 20 minutes at a temperature of about 50° C. to about 58° C.;
applying a vacuum of at least −0.070 MPa and mixing the first mixture for at least 5 minutes;
combining at least one abrasive to the first mixture to make a second mixture;
mixing the second mixture for at least 10 minutes;
applying a vacuum of at least −0.08 MPa to the second mixture;
combining at least one surfactant to the second mixture to make a third mixture;
mixing the third mixture for at least 5 minutes at a temperature of at least 45° C.;
releasing the vacuum over the third mixture;
stopping mixing of the third mixture;
combining at least one zinc compound, at least one flavoring agent, and at least one additive to the third mixture to make a fourth mixture;
mixing the fourth mixture for at least 3 minutes;
applying vacuum of at least −0.092 MPa to the fourth mixture; and
mixing the fourth mixture for at least 10 minutes to make the dentifrice composition, wherein the dentifrice composition is a toothpaste as in claim 5.

11. The method of making a dentifrice composition as in claim 10, wherein the at least one liquid medium comprises water, wherein the at least one liquid medium is present in an amount from about 42 wt % to about 46 wt %, based on the total weight of the dentifrice composition;
wherein the at least one humectant comprises sorbitol and glycerin, wherein the at least one humectant is present in an amount from about 18 wt % to about 22 wt %, based on the total weight of the dentifrice composition;
wherein the at least one thickening agent comprises carboxymethyl cellulose, tetrasodium pyrophosphate, and xanthan gum, wherein the thickening agents is present in an amount from about 0.8 wt % to about 2 wt %, based on the total weight of the dentifrice composition;
wherein the at least one flavoring agent is present in an amount from about 0.8 wt % to about 1.2 wt %, based on the total weight of the dentifrice composition;
wherein the at least one surfactant comprises sodium lauryl sulfate, wherein the at least one surfactant is present in an amount from about 1.6 wt % to about 2.2 wt %, based on the total weight of the dentifrice composition;
wherein the at least one sweetening agent comprises sodium saccharin, wherein the at least one sweetening agent is present in an amount from about 0.2 wt % to about 1 wt %, based on the total weight of the dentifrice composition;
wherein the at least one anti-caries agent comprises sodium monofluorophosphate, wherein the at least one anti-caries agent is present in an amount from about 0.8 wt % to about 1.4 wt %, based on the total weight of the dentifrice composition; and
wherein the at least one additive comprises betaine and benzyl alcohol, wherein the at least one additive is present in an amount from about 0.5 wt % to about 5 wt %, based on the total weight of the dentifrice composition.

12. The method of making a dentifrice composition as in claim 10, wherein the zinc citrate trihydrate and zinc oxide are in a weight ratio of about 1:2.

13. The method of making a dentifrice composition as in claim 10, wherein the additives further comprises a coloring agent, a preservative, and a base.

14. A toothpaste comprising:
an alginate present in an amount from about 0.01 wt % to about 1.2 wt %, based on the total weight of the toothpaste;
zinc compounds present in an amount from about 0.1 wt % to about 2 wt %, based on the total weight of the toothpaste, wherein the zinc compounds comprise zinc oxide and zinc citrate trihydrate, the zinc citrate trihydrate and the zinc oxide being present in a weight ratio of about 1:1 to about 1:4; and an abrasive comprising calcium carbonate,
wherein the toothpaste does not contain a polyphosphate and wherein the toothpaste is free of nonionic surfactants.

15. The toothpaste of claim 14, wherein the abrasive is present in an amount from about 18 wt % to about 26 wt %, based on the total weight of the toothpaste.

16. The toothpaste of claim 14, wherein the abrasive is present in an amount from about 38 wt % to about 50 wt %, based on the total weight of the toothpaste.

17. The toothpaste of claim 14 further comprising a humectant comprising glycerin, sorbitol, polyethylene glycol, or a combination thereof.

18. The toothpaste of claim 14 further comprising a thickening agent selected from carboxymethyl cellulose, xanthan gum, carrageenan gum, and a combination of two or more thereof.

19. The toothpaste of claim 18, wherein the thickening agent is present in an amount from about 1 wt % to about 4 wt %, based on the total weight of the toothpaste.

* * * * *